United States Patent
Nafpliotis

(10) Patent No.: US 6,171,274 B1
(45) Date of Patent: Jan. 9, 2001

(54) BIOMECHANICAL SUIT

(76) Inventor: Harry Nafpliotis, 15 Rising Ridge Rd., Upper Saddle River, NJ (US) 07548

(*) Notice: Under 35 U.S.C. 154(b), the term of this patent shall be extended for 0 days.

(21) Appl. No.: 09/303,617

(22) Filed: Mar. 11, 1999

(51) Int. Cl.[7] .................................................. A61L 15/00
(52) U.S. Cl. ............................................. 602/75; 602/76
(58) Field of Search .............................. 602/75, 76, 77, 602/78; 482/105, 125; 128/169

(56) References Cited

U.S. PATENT DOCUMENTS 3,613,679 * 10/1971 Bijou .
5,555,562 * 9/1996 Holt et al. .
5,720,042 * 2/1998 Wilkinson .
5,754,982 * 5/1998 Gainer .
5,779,659 * 7/1998 Allen .

* cited by examiner

Primary Examiner—Michael A. Brown
Assistant Examiner—Lalita M. Hamilton
(74) Attorney, Agent, or Firm—Richard A. Joel, Esq

(57) ABSTRACT

A biomechanical suit comprises a mini-shirt and shorts connected front and rear by suspenders. The shirt starts proximally from the level of cervical three vertebra (C-3) and extends down to the eighth thoracic vertebra (T8) and includes a zipper from T8–C3. Two spaced front suspenders are mounted to the lower edge of the shirt and are adjustably coupled to the shorts. The rear suspenders are attached proximally and distally a predetermined distance bilaterally from the vertebral column. The distal attachment is through a tensiometer which adjusts the tension to correct unusual kyphotic or scoliotic conditions.

6 Claims, 3 Drawing Sheets

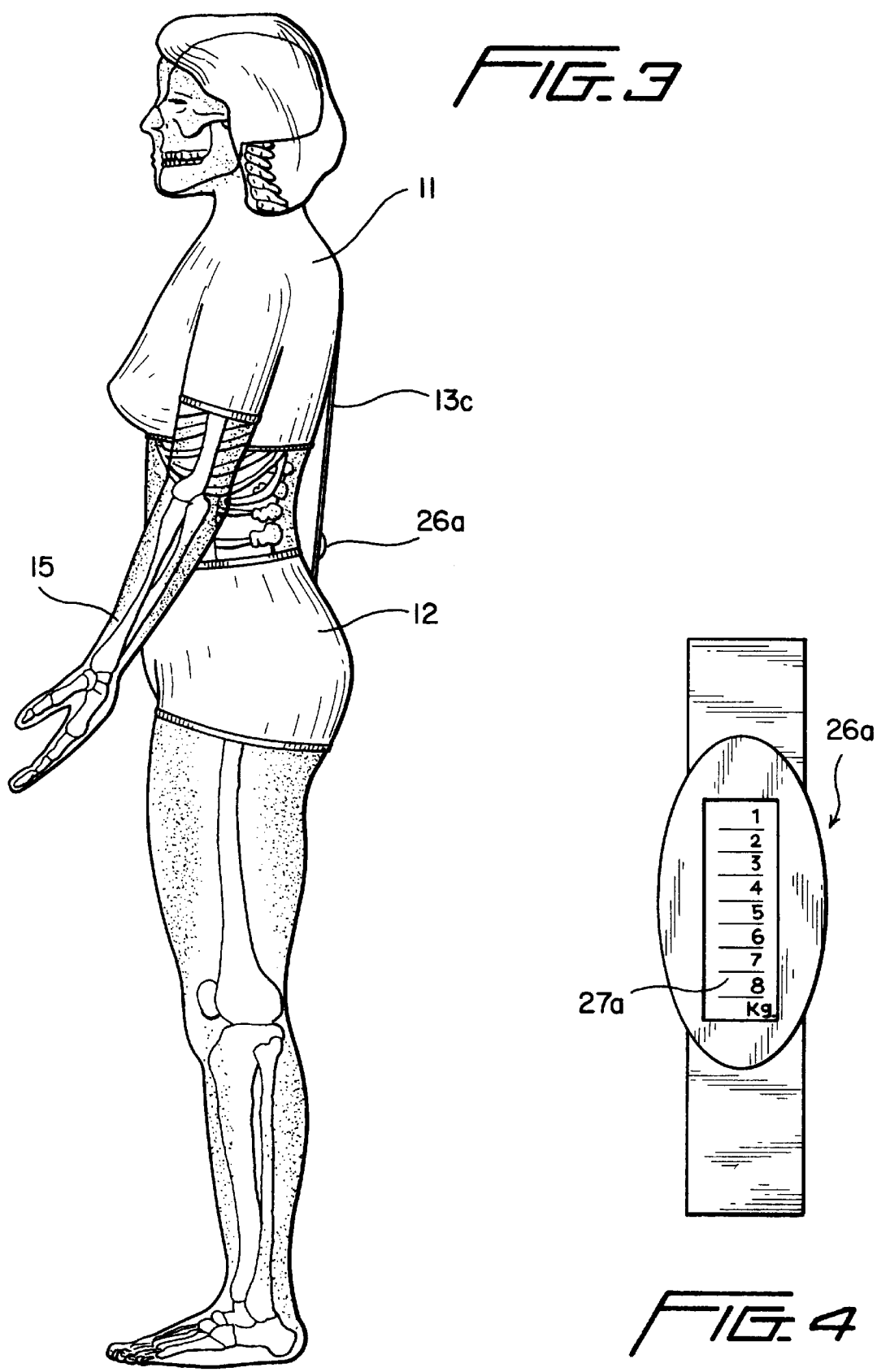

BIOMECHANICAL SUIT

CROSS-REFERENCE TO RELATED APPLICATIONS

None

STATEMENT REGARDING FEDERALLY SPONSORED RESEARCH OR DEVELOPMENT

Not applicable

BACKGROUND OF THE INVENTION

FIELD OF THE INVENTION

This invention relates to a two piece biomechanical suit which is intended to correct physical conditions without extensive surgery and/or progressive casting.

DESCRIPTION OF THE RELATED ART INCLUDING INFORMATION DISCLOSED UNDER 37 CFR §§1.97–1.98

In the prior art, the solution to scoliotic, kyphotic and/or young children's spinal conditions often involved extensive surgery which was at the very least somewhat risky and may or may not have been effective. Another treatment for such conditions involved progressive casting which was incapacitating and uncomfortable. Further problems of casting include muscle waste, skin break-down, and lack of cleanliness. The casting was either used alone or in conjunction with surgery.

In contrast to the prior art, applicant's biomechanical suit has been designed to enhance correct body mechanics, condition upper and lower extremities musculature, improve cardiovascular fitness and correct poor spinal posture. The invention is intended to correct unusual kyphotic and/or scoliotic conditions particularly those that have progressed with age such as osteoporosis. The use of applicant's biomechanical suit is effective and far less costly than present treatments. The use of the suit is also not incapacitating which is a prime objection to surgery and casting. Many individuals forego treatment rather than be incapacitated with no guarantee of results.

SUMMARY OF THE INVENTION

This invention relates to biomechanical suits and particularly to a two piece suit having tension adjusting means to correct unusual kyphotic and/or scoliotic conditions.

The biomechanical suit includes a mini-shirt and shorts which are connected by suspenders in the front and rear. The front suspenders are adjusted only once and are joined at their ends to the shirt and shorts by Velcro® fasteners or other materials enhancing strong attachments. The rear suspenders are attached by Velcro® fasteners approximately two inches bilaterally from the vertebral column along the medial borders of both scapulas at the upper end. The lower end of the rear suspenders is attached approximately two inches bilaterally to the vertebral column from the fourth lumbar vertebra (L4) down to the sacral area. The lower suspender ends are attached to a fastener through a tensiometer which is used to set the desired tension to correct the individual's posture problem.

The mini-shirt includes a front zipper for ease of wearing and removal. The min-shirt has short sleeves and along with the shorts, is made of a material such as neoprene, Spandex®, or, Lycra® or polyester (combination with fleece and nylon). This latter material provides horizontal flexibility but not vertical. The suit is thus rather comfortable and with the tension adjustment is able to correct physical posture problems without surgery or long term casting.

Accordingly, an object of this invention is to provide a new and improved biomechanical suit to correct physical posture problems.

Another object of this invention is to provide a new and improved two piece biomechanical suit which includes front suspenders and adjustable rear suspenders to apply a specific tension to correct the wearer's posture problem.

Additionally, in view of the adjustable tension, another object of this invention is to provide relief from painful spinal conditions resulting from poor posture mechanics.

A further object of this invention it to provide a new and improved two piece biomechanical suit including rear suspenders which are connected to the shorts through tensiometers which measure the amount of tension applied to the wearer.

A more specific object of this invention is to provide a new and improved two piece biomechanical suit including front and rear suspenders which are adjustably mounted to predetermined positions on the suit and include tension measuring means at the lower end of the rear suspenders so that said suspenders may be adjusted to provide the necessary tension to correct the wearer's physical problem.

BRIEF DESCRIPTION OF THE DRAWINGS

The above and other objects and advantages of this invention may be more clearly seen when viewed in conjunction with the accompanying drawings wherein:

FIG. 3 is a lateral view of the invention; and,

FIG. 4 is an exploded view of the tensiometer used in the invention.

DETAILED DESCRIPTION OF THE INVENTION

Figure 1:
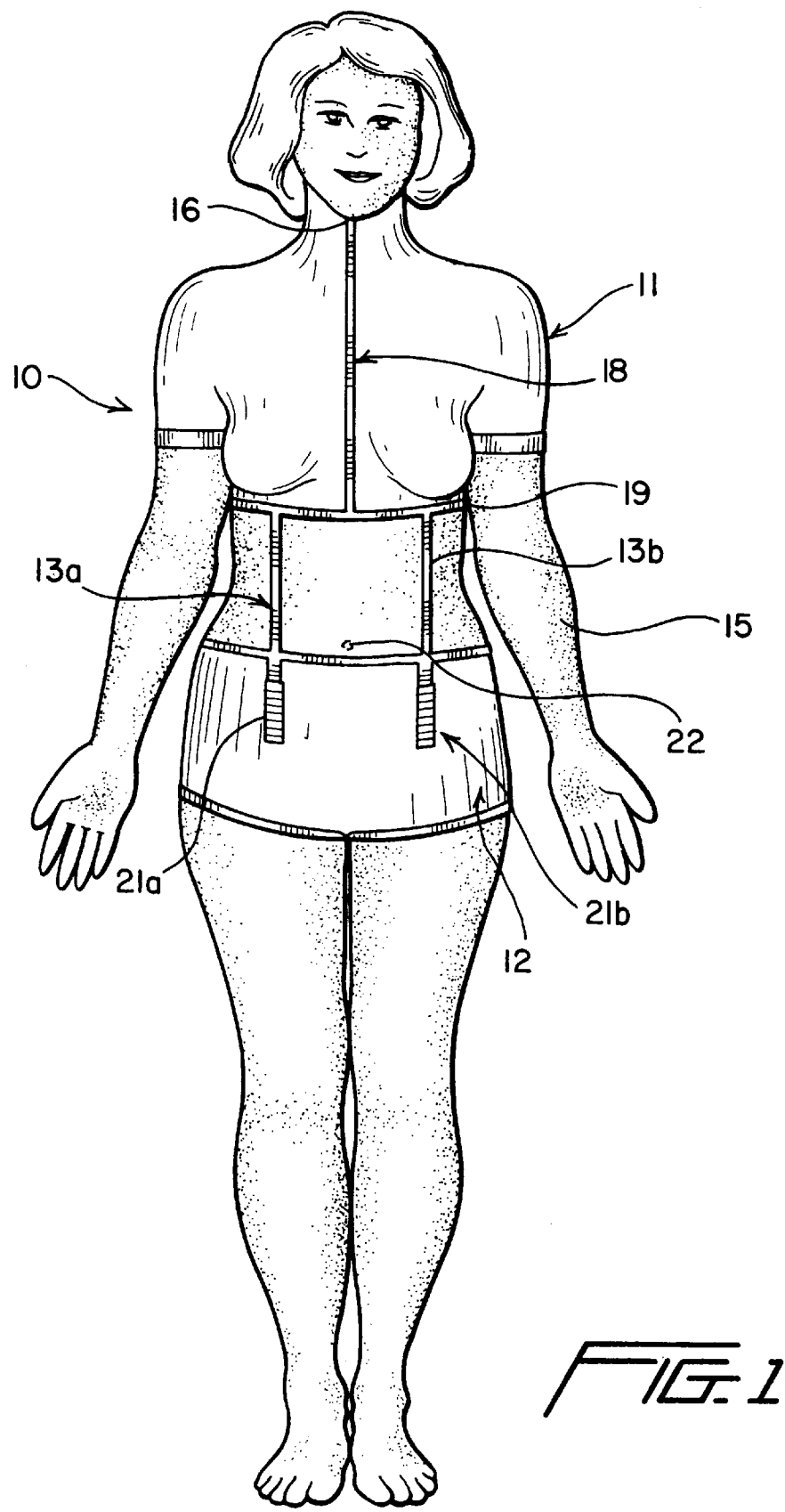
FIG. 1 is a front or anterior view of the invention.

Referring now to the drawings, the invention as shown in FIG. 1, comprises a two piece biomechanical suit 10 worn by an individual 15. Essentially, the suit comprises a mini-shirt 11 connected to shorts 12 by suspenders 13*a–d*. The suit 10 may be made of a material such as neoprene, Spandex, Lycra or canvas or polyester (combination fleece and nylon). This latter material provides horizontal flexibility (stretching), but not vertical.

The short sleeved mini-shirt 11 starts proximally from the level of cervical three vertebra (C3) 16 and extends down to eighth thoracic vertebra (T8) 17. The front enclosure is fastened with a zipper 18 for ease of use. The two front suspenders 13*a* and 13*b* are fastened two inches laterally from the xiphoid process of the proximal end at the base 19 of the shirt 11 and extend to the distal vertical fastener attachments 21*a* and 21*b*. The attachments 21*a*, 21*b*, which may be Velcro® fasteners, are positioned three inches bilaterally of the umbilicus 22.

Figure 2:
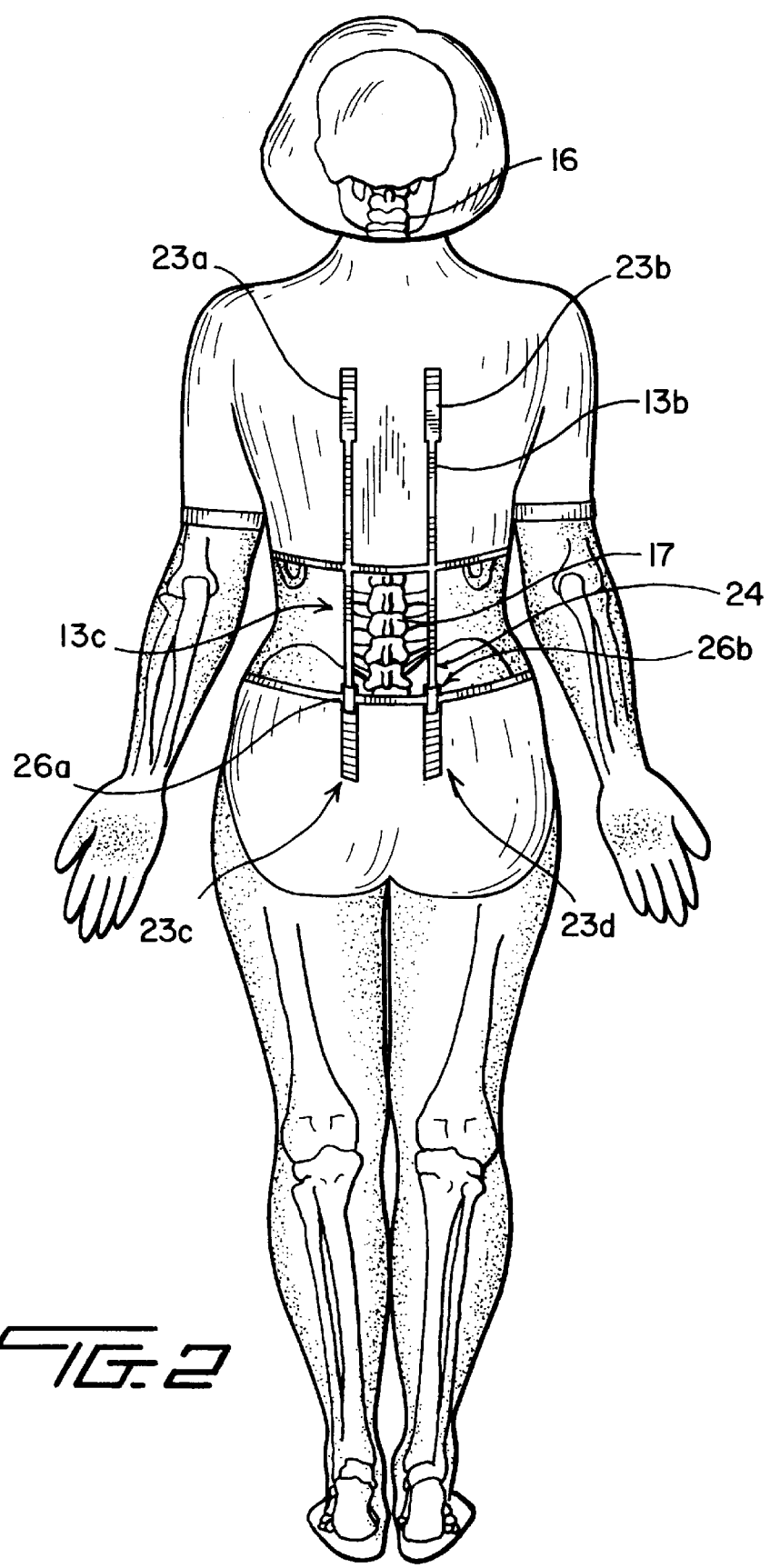
FIG. 2 is a rear or posterior view of the invention.

The back or posterior enclosures, best seen in FIG. 2, include two suspenders 13c and 13*d* attached to vertical fasteners 23*a* and 23*b* proximately and 23*c* and 23*d* distally at the desired level. Both proximal and distal fasteners 23*a–d* are attached approximately two inches bilaterally from the vertebral column 24 along the medial borders of both scapulas and are attached distally, approximately two inches bilaterally to the vertebral column 24 from the fourth lumbar vertebra (L-4) down to the sacral area. Each suspender 13c and 13d is attached distally to a fastener 21c and 21d through tensiometer 26a and 26b respectively.

The suspenders 13a–13d are made of firm elastic durable material similar to commercial suspenders which provide considerable tension during adjustments at training sessions. The suspenders 13a–13d must be strong enough to be used jointly with Velcro® fasteners or other material enhancing firmness for each attachment.

The tensiometers 26a, 26b which are best shown in the exploded view of FIG. 4, are made of light aluminum. The devices 26a, 26b provide a scale 27a, 27b for measuring tension in kilograms. The tensiometers 26a, 26b are only used in conjunction with the rear suspenders 13c and 13d. The front suspenders 13a, 13b are adjusted only once to provide a counterbalance to the back tension applied by the rear suspenders 13c, 13d. The front suspenders 13a, 13b are made of elastic or non-elastic straps fixed proximately and connected with Velcro® enclosures 21a, 21b, or other material enhancing firmness and precise position during stretching.

The Velcro® enclosures 21a–21d are one to two inches in width depending upon the necessary tension. The required tension is determined by an individual's size and fitness as well as the particular unacceptable level of training and/or poor posture such as unusual kyphotic and/or scoliotic conditions that have progressed with age or disease, for example, osteoporosis. In correcting scoliotic conditions, specific tensiometric adjustments will be necessary. These adjustments may be measured by the tensiometer 26a and 26b and achieved by tightening the suspenders 13c and 13d.

The biomechanical suit 10 as thus described is easily removed, adjusted and replaced. Long term casting which can range from six months to seventeen months is avoided as well as the attendant problems of muscle waste, skin-breakdown and lack of cleanliness. The suit 10 also helps individuals to attain their exercise goals by adhering to fitness programs and working harder and longer while having fun. These enhancement factors, easily adjustable and removable may all contribute to the patients ability to participate earlier and be more attentive in his or her rehabilitation program.

While the invention has been explained by a detailed description of certain specific embodiments, it is understood that various modifications and substitutions can be made in any of them within the scope of the appended claims which are intended also to include equivalents of such embodiments.

What is claimed, is:

1. A one piece biomechanical body suit worn by individuals to correct physical posture problems comprising:

a mini-shirt having a front and rear and commencing proximally from the level of the cervical three vertebra (C-3) and extending down to the eighth thoracic vertebra (T-8) and including a zipper on the front thereof extending from C-3 to T-8;

a pair of shorts;

a pair of spaced front suspenders affixed at one end to the mini-shirt and adjustably coupled to the shorts at the other end;

a pair of spaced rear suspenders having upper and lower ends and each mounted along the medial borders of a scapula at their upper end; and a tensiometer mounted adjacent the lower end of each suspender to measure tension applied and an adjustable fastener mounted on the lower end in the sacral area to permit attachment to the shorts.

2. A one piece biomechanical body suit worn by individuals to correct physical posture problems in accordance with claim 1, wherein:

the rear suspenders are each attached to the suit approximately two inches bilaterally to the vertebral column from the fourth lumbar vertebra (1–4) to the sacral area.

3. A one piece biomechanical body suit worn by individuals to correct physical posture problems in accordance with claim 2, wherein:

the mini-shirt includes a base and the front suspenders are fastened to said base and said suspenders extend downwardly to the shorts where they are fastened a predetermined distance bilaterally of the umbilicus, wherein said suspenders are adjustable to correct posture and to provide relief from painful spinal conditions resulting from poor posture mechanics.

4. A one piece biomechanical body suit worn by individuals to correct physical posture problems in accordance with claim 3, wherein:

the front suspenders are fastened two inches laterally of the xiphoid process at the upper end and include adjustable hook and loop® fasteners at the other end and said shorts including mating Velcr® fasteners to connect with said suspender fasteners.

5. A one piece biomechanical body suit worn by individuals to correct physical posture problems in accordance with claim 3, wherein:

the front suspenders are positioned three inches bilaterally of the umbilicus at their lower end.

6. A one piece biomechanical body suit worn by individuals to correct physical posture problems in accordance with claim 1, wherein:

the tensiometers each include a scale to permit a tension reading for adjustment purposes.

* * * * *